US007596404B2

(12) United States Patent
Maier et al.

(10) Patent No.: US 7,596,404 B2
(45) Date of Patent: Sep. 29, 2009

(54) METHOD OF CHEMICAL IMAGING TO DETERMINE TISSUE MARGINS DURING SURGERY

(75) Inventors: John S. Maier, Pittsburgh, PA (US);
Shona Stewart, Pittsburgh, PA (US);
Jeffrey Cohen, Pittsburgh, PA (US);
Matthew Nelson, Harrison City, PA (US)

(73) Assignee: ChemImage Corporation, Pittsburgh, PA (US)

( * ) Notice: Subject to any disclaimer, the term of this patent is extended or adjusted under 35 U.S.C. 154(b) by 0 days.

(21) Appl. No.: 11/361,256

(22) Filed: Feb. 24, 2006

(65) Prior Publication Data

US 2006/0155195 A1 Jul. 13, 2006

Related U.S. Application Data

(63) Continuation-in-part of application No. 11/204,196, filed on Aug. 9, 2005, which is a continuation of application No. 10/184,580, filed on Jun. 28, 2002, now Pat. No. 6,965,793, and a continuation of application No. 10/185,090, filed on Jun. 28, 2002, now Pat. No. 6,954,667.

(60) Provisional application No. 60/656,057, filed on Feb. 24, 2005, provisional application No. 60/301,708, filed on Jun. 28, 2001.

(51) Int. Cl.
*A61B 6/00* (2006.01)
(52) U.S. Cl. .................. 600/476; 600/477; 600/473
(58) Field of Classification Search ................ 600/477, 600/476, 473
See application file for complete search history.

(56) References Cited

U.S. PATENT DOCUMENTS

| 5,194,912 | A | | 3/1993 | Batchelder et al. |
| 5,261,410 | A | | 11/1993 | Alfano et al. |
| 5,377,004 | A | | 12/1994 | Owen et al. |
| 5,442,438 | A | | 8/1995 | Batchelder et al. |
| 5,539,517 | A | | 7/1996 | Cabib et al. |
| 5,596,992 | A | * | 1/1997 | Haaland et al. ............. 600/473 |

(Continued)

FOREIGN PATENT DOCUMENTS

WO PCT/US2006/006663 8/2006

OTHER PUBLICATIONS

Chandler, W. F., et al., "Intraoperative Use of Real-time Ultrasonography in Neurosurgery," J. Neurosurg (1982) pp. 157-163, vol. 57.

(Continued)

*Primary Examiner*—Eric F Winakur
*Assistant Examiner*—Helene Bor
(74) *Attorney, Agent, or Firm*—Morgan Lewis & Bockius LLP

(57) ABSTRACT

A method and system to differentiate a tissue margins during various medical procedures. A region containing a biological tissue is irradiated, with a substantially monochromatic light. Raman spectroscopic data is obtained from the irradiated region. A boundary between a neoplastic portion and a non-neoplastic portion, in the region containing the biological tissue, is differentiated by evaluating the Raman spectroscopic data for at least one Raman spectroscopic value characteristic of either the neoplastic portion or the non-neoplastic portion. The neoplastic portion is selected for physical manipulation based on the differentiation of the boundary between the neoplastic portion and the non-neoplastic portion.

23 Claims, 6 Drawing Sheets

U.S. PATENT DOCUMENTS

| | | | |
|---|---|---|---|
| 5,623,342 | A | 4/1997 | Baldwin et al. |
| 5,689,333 | A | 11/1997 | Batchelder et al. |
| 5,733,739 | A * | 3/1998 | Zakim et al. ................... 435/29 |
| 5,769,081 | A * | 6/1998 | Alfano et al. ............... 600/476 |
| 5,891,619 | A * | 4/1999 | Zakim et al. ................... 435/4 |
| 6,002,476 | A * | 12/1999 | Treado ........................ 356/301 |
| 6,151,522 | A * | 11/2000 | Alfano et al. ............... 600/473 |
| 6,205,354 | B1 * | 3/2001 | Gellermann et al. ........ 600/477 |
| 6,571,118 | B1 * | 5/2003 | Utzinger et al. ............. 600/476 |
| 6,640,132 | B1 | 10/2003 | Freeman et al. |
| 6,665,556 | B1 * | 12/2003 | Alfano et al. ............... 600/473 |
| 6,741,884 | B1 | 5/2004 | Freeman et al. |
| 6,937,885 | B1 | 8/2005 | Lewis et al. |
| 2002/0007123 | A1 * | 1/2002 | Balas .......................... 600/476 |
| 2004/0038320 | A1 * | 2/2004 | Banerjee .................... 435/7.23 |
| 2004/0152992 | A1 * | 8/2004 | Zeng .......................... 600/476 |
| 2005/0240107 | A1 * | 10/2005 | Alfano et al. ............... 600/476 |
| 2006/0013454 | A1 * | 1/2006 | Flewelling et al. .......... 382/128 |
| 2006/0155195 | A1 * | 7/2006 | Maier et al. ................. 600/476 |
| 2006/0250613 | A1 * | 11/2006 | Demuth et al. .............. 356/301 |
| 2006/0253261 | A1 * | 11/2006 | Maier et al. ..................... 702/19 |
| 2006/0269972 | A1 * | 11/2006 | Smith et al. ................. 435/7.23 |
| 2006/0281068 | A1 * | 12/2006 | Maier et al. ..................... 435/4 |
| 2007/0093708 | A1 * | 4/2007 | Benaron et al. ............. 600/407 |

OTHER PUBLICATIONS

Poon, W. S., et al., "Laser-Induced Fluorescence: Experimental Intraoperative Delineation of Tumor Resection Margins," J. Neurosurg (1992) pp. 679-686, vol. 76.

Hansen, D. A., et al., "Indocyanine Green (ICG) Staining and Demarcation of Tumor Margins in a Rat Glioma Model," Surgical Neurol. (1993) pp. 451-456, vol. 40.

Haglund, M. M. et al., "Enhanced Optical Imaging of Rag Gliomas and Tumor Margins," Neurosurgery (1994) pp. 930-941, vol. 35, No. 5.

Yuan, X., et al., "Isolation of Cancer Stem Cells from Adult Glioblastoma Multiforme," Oncogene (2004) pp. 9392-9400, vol. 23.

Ahmad, K., "Small Subsets of Cells Initiate Brain Tumors," Lancet Oncology (2005) pp. 9, vol. 6.

Dirks, P. B., "Brain Tumor Stem Cells," Biology of Blood Marrow Transplantation (2005) pp. 12-13, vol. 11.

Bakker Schut, T.C., et al., "Real-Time Tissue Characterization on the Basis of in vivo Raman Spectra," Journal of Raman Spectroscopy (2002) pp. 580-585, vol. 33.

Dong, J., et al., "Metal Binding and Oxidation of Amyloid-B Within Isolated Senile Plaque Cores: Raman Microscopic Evidence," Biochemistry (2003) pp. 2768-2773, vol. 42.

Frank, C. J., et al., "Characterization of Human Breast Biopsy Specimens with Near-IR Raman Spectroscopy," Analytical Chemistry, (1994) pp. 319-326, vol. 66.

Haka, A. S., et al., "Identifying Microcalcifications in Benign and Malignant Breast Lesions by Probing Differences in Their Chemical Composition Using Raman Spectroscopy," Cancer Research (2002) pp. 5375-5380, vol. 62.

Hanlon, E. B., et al., "Prospects for In Vivo Raman Spectroscopy," Phys. Med. Biol. (2000) pp. R1-R59, vol. 45.

Lakshmi, R. J., et al., "Tissue Raman Spectroscopy for the Study of Radiation Damage: Brian Inradiation of Mice," Radiation Research (2002) pp. 175-182, vol. 157.

Liu, C. H. et al., "Near-IR Fourier Transform Raman Spectroscopy of Normal and Atherosclerotic Human Aorta," Lasers in Life Science (1992) pp. 257-264, vol. 4.

Miura, T., et al., "Binding Mode of Congo Red to Alzheimer's Amyloid B-peptide Studied by UV Raman Spectroscopy," Journal of Raman Spectroscopy (2002) pp. 530-535, vol. 33.

Mizuno, A., et al., "Near Infrared FT-Raman Spectra of the Rat Brain Tissues," Neuroscience Letters (1992) pp. 47-52, vol. 141.

Mizuno, A., et al., "Near Infrared Fourier Transform Raman Spectroscopic Study of Human Brain—Tissues and Tumors," Journal of Raman Spectroscopy (1994) pp. 25-29, vol. 25.

Naumann, D., "FT-Infrared and FT-Raman Spectroscopy in Biomedical Research," Applied Spectroscopy Reviews (2001) pp. 239-289, vol. 36.

Petrich, W., "Mid-Infrared and Raman Spectroscopy for Medical Diagnostics," Applied Spectroscopy Reviews (2001) pp. 181-237, vol. 36.

Sajid, J., et al., "Fourier Transform Vibrational Spectroscopic Analysis of Human Cerebral Tissue," Journal of Raman Spectroscopy (1997) pp. 165-169, vol. 28.

Boppart, S. A., et al., "Opticall Coherence Tomography for Neurosurgical Imaging of Human Intracortical Melanoma," Neurosurgery (1998) pp. 834-841, vol. 43.

* cited by examiner

METHOD OF CHEMICAL IMAGING TO DETERMINE TISSUE MARGINS DURING SURGERY

RELATED APPLICATIONS

This application claims priority to U.S. Provisional Patent Application No. 60/656,057, filed Feb. 24, 2005 which is incorporated herein by reference in its entirety. This application is a continuation-in-part of U.S. patent application Ser. No. 11/204,196, filed Aug. 9, 2005 which is a continuation of U.S. Ser. No. 10/184,580 now U.S. Pat. No. 6,965,793, filed Jun. 28, 2002 and a continuation of U.S. Ser. No. 10/185,090 now U.S. Pat. No. 6,954,667, filed Jun. 28, 2002, both of which claim priority to U.S. Provisional Patent Application No. 60/301,708, filed Jun. 28, 2001, each of which is incorporated herein by reference in its entirety.

FIELD OF THE DISCLOSURE

This application relates to the evaluation of biological tissue to differentiate the margin of neoplastic tissue from the margin of non-neoplastic tissue, using Raman spectroscopy.

BACKGROUND

The detection of tissue margins to surgically remove tumors is highly subjective. Medical personnel would greatly benefit from methods for the quantitative identification of margins, between neoplastic and non-neoplastic tissue, to assure that sufficient tissue near the tumor is surgically removed thereby preventing the reoccurrence of the tumor. Brain tissue is a particularly important case where ill-defined margins may disrupt important functions of the brain.

Current operative microscope methods are inadequate for the intra-operative differentiation of primary central nervous system neoplastic tissue from non-neoplastic tissue. Digital image guidance techniques are hampered by the problems of structural shift which occurs during resection such that the pre-operative images do not correlate to the operative field. Ultrasonographic methods have limitations associated with tissue swelling or the presence of hemorrhage. Neurosurgical investigators have used various injectable dyes or stains to demark tumor margins to resolve the problems associated with the current methods. These injectable agents demarcate boudaries which are limited to a physical process, the breakdown of the blood-brain barrier, rather than identifying specific neoplastic boundaries.

Various researchers have applied Raman spectroscopy to characterize a wide variety of biological tissue as described in: Hanlon et. al., 2000, Physics in Medicine and Biology, 45: R1-R59; Lakshmi et al., 2002, Radiation Research, 157(2), 175-182; Mizuno et al., 1992, Neuroscience Letters, 141 (1), 47-52; Mizuno et al., 1994, Journal of Raman Spectroscopy, 25, 25-29; Sajid et al., 1997, Journal of Raman Spectroscopy, 28, 165-169; Dong et al., 2003, Biochemistry, 42, 2768-2773; and Mirura et al., Journal of Raman Spectroscopy, 2002, 33, 530-535, each of which is incorporated by reference in its entirety.

In the case of brain tissue, Raman spectroscopy has been performed on the cerebral cortex, white matter of the cerebrum and the thalamus, using near infrared illumination. The intensity ratios of the amide I bands compared to bands representative of CH bonds were used to differentiate between grey and white matters. These intensity ratios were also used to distinguish between normal brain tissue and brain tumor. Other studies have shown changes in the Raman spectra of biological and brain tissue of mice after the mice were subjected to irradiation. Raman spectroscopy has also been used to monitor amyloid β-plaques deposited in the brains with Alzheimer's disease ("AD"). Using NIR illumination, clear differences between the Raman spectra of AD tissue and non-diseased tissue were observed. Features of the Raman spectrum appear indicative of β-pleated sheet conformation were observed for amyloid β-protein in senile plaques. The lipid-to-protein intensity ratios were used to monitor disease-related changes in the tissue composition.

SUMMARY

The present disclosure provides for a system and method to differentiate tissue margins during various medical procedures. A region containing a biological tissue is irradiated, with a substantially monochromatic light. Raman spectroscopic data is obtained from the irradiated region. A boundary between a neoplastic portion and a non-neoplastic portion, in the region containing the biological tissue, is differentiated by evaluating the Raman spectroscopic data for at least one Raman spectroscopic value characteristic of either the neoplastic portion or the non-neoplastic portion. The neoplastic portion is selected for physical manipulation based on the differentiation of the boundary between the neoplastic portion and the non-neoplastic portion. In one embodiment, the step of differentiating a boundary between neoplastic portion and non-neoplastic portion in the irradiated region includes correlating the Raman spectral data with a visible image of the same region. In one embodiment, the selected tissue is physically manipulated. In another embodiment, the biological tissue is neurological tissue.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings.

DETAILED DESCRIPTION OF THE EMBODIMENTS

Figure 1:
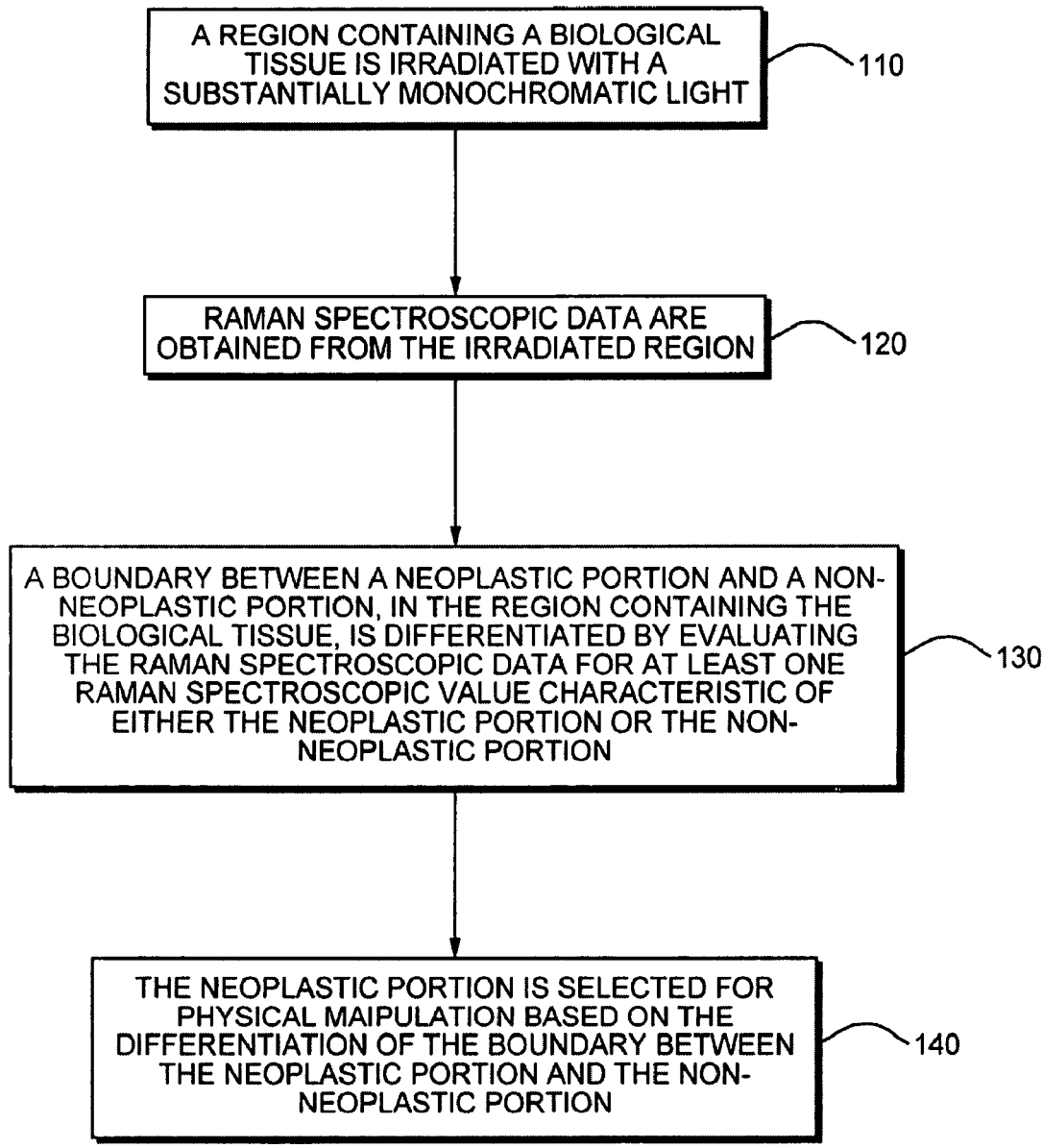
FIG. 1 is a flow chart illustrating an embodiment of the present disclosure.

Reference will now be made in detail to the embodiments of the present disclosure, examples of which are illustrated in the accompanying drawings. Wherever possible, the same reference numbers will be used throughout the drawings to refer to the same or like parts.

The present disclosure provides for a method to differentiate tissue margins during various medical procedures. Raman spectroscopy will be used to differentiate the margins of neoplastic and non-neoplastic biological tissue. This will be accomplished by detection of molecules indicative of neoplastic and non-neoplastic tissue. In one embodiment, the inventors will use Raman chemical imaging to identify the neoplastic and non-neoplastic tissue. The Raman spectra and Raman images will be molecule-specific and thus more specific than images derived from stains.

Differences, in the Raman spectra of molecules and tissue within biological tissue, in an irradiated region, will be used to differentiate boundaries of neoplastic from non-neoplastic tissue. The ability to differentiate these boundaries results from the presence of endogenous molecules, within the tissue, that are indicative of a boundary between neoplastic portion and non-neoplastic tissue. The Raman spectral data may be collected using non-imaging Raman microspectroscopy or as spatially resolved independent Raman spectra at various Raman shift values. The spatially resolved Raman spectra may be collected in at least one direction. In a typical Raman chemical imaging experiment, a specimen is illuminated with monochromatic light, and the Raman scattered light is filtered by an imaging spectrometer which passes only a single wavelength range. The Raman scattered light may then be used to form an image of the specimen. A spectrum is generated corresponding to millions of spatial locations at the sample surface by tuning an imaging spectrometer over a range of wavelengths and collecting images intermittently. Changing the selected band pass (wavelength) of the imaging spectrometer to another appropriate wavelength causes a different material to become visible. A series of such images can then uniquely identify constituent materials, and computer analysis of the image is used to produce a composite image highlighting the information desired. Although Raman chemical imaging is predominately a surface technique, depth-related information can also be obtained by using different excitation wavelengths or by capturing chemical images at incremental planes of focus. Contrast is generated in the images based on the relative amounts of Raman scatter or other optical phenomena such as luminescence that is generated by the different species located throughout the sample. Since a spectrum is generated for each pixel location, chemometric analysis tools such as correlation analysis, Principle Component Analysis (PCA) and factor rotation, including Multivariate Curve Resolution (MCR) can be applied to the image data to extract pertinent information otherwise missed by ordinary univariate measures.

Several Raman chemical imaging ("RCI") technologies have evolved including point scanning RCI, line imaging RCI, liquid crystal tunable filters RCI and fiber array spectral translator ("FAST") technology.

Raman spectroscopy may be coupled with other imaging techniques to aid in the differentiation of neoplastic tissue from non-neoplastic tissue. These imaging techniques include transmission or reflectance modes; fluorescence; photoluminescence; chemiluminescence; and electroluminescence imaging. The Raman spectrometer may also operate in conjunction with polarized light microscopy and/or differential interference contrast imaging.

In one embodiment, the entire field of view to be investigated is illuminated simultaneously using an approach called wide-field illumination. This illumination strategy yields Raman scattered light from each point within the field of view simultaneously. Measurement of this Raman scattered light from each point within the field can be accomplished by using a set of collection optics to collect the light emanating from the field of view. The collected light is filtered, using optical components, to provide Raman scattered light preferentially to a detector. Optical components used to filter the collected light include combinations of band pass and band rejection filters. For example a band rejection filter is used to reject the substantially monochromatic illumination light. Simple band pass filters can be used to preferentially select the Raman scattered light for detection, however, a preferred approach is to use a tunable filter to select light at a series of Raman shifts from the wavelength of illumination. Raman spectroscopic data from the field of view is frequently structured as what is known in the art as an image hypercube which is a series of 2 dimensional images at different points in spectral space. Each pixel in such a hypercube represents a spectrum of the position in the measured field of view over the spectral variable chosen for the measurement.

With reference to FIG. 1, a region containing a biological tissue is irradiated, with a substantially monochromatic light, in step 110. In step 120, Raman spectroscopic data is obtained from the irradiated region. In step 130, a boundary between a neoplastic portion and a non-neoplastic portion, in the region containing the biological tissue, is differentiated by evaluating the Raman spectroscopic data for at least one Raman spectroscopic value characteristic of either the neoplastic portion or the non-neoplastic portion. In step 140, the neoplastic portion is selected for physical manipulation based on the differentiation of the boundary between the neoplastic portion and the non-neoplastic portion. In one embodiment, the steps of irradiating, obtaining, differentiating and selecting takes place in vivo on a region of biological tissue of a patient. The Raman spectroscopic value includes a Raman shift for one of the following the neoplastic portion and the non-neoplastic portion.

In one embodiment, the step of differentiating a boundary between neoplastic portion and non-neoplastic portion in the irradiated region includes correlating the Raman spectral data with a visible image of the same region. A means for correlating the visible image and the Raman spectral data includes fusing the images using software. While Raman detector and visible cameras often generate images having differing contrast, the sample fields of view can be matched through a combination of optical and software manipulations. As a result, the Raman spectral data and visible images can be compared and even fused through the use of overlay techniques and correlation techniques to provide the user a near-real time view of both detector outputs on the same computer display. The comparative and integrated views of the sample can significantly enhance the understanding of sample morphology and architecture. By comparing the visible images and Raman spectral data, additional useful information can be acquired about the chemical composition, structure and concentration of species in samples.

In one embodiment, the method further comprises physically manipulating one of the neoplastic portion and the non-neoplastic portion. The physically manipulating the neoplastic portion may comprise excising the neoplastic portion from the region containing said biological tissue.

In another embodiment of the present disclosure, the method may further comprise differentiating, selecting, and excising the selected neoplastic portion are performed iteratively. The steps of differentiating, selecting and excising the selected neoplastic portion are performed iteratively may also take place in vivo on a region of biological tissue of a patient. In another embodiment, the present invention may further comprise rinsing the region containing biological tissue between the steps of selecting and excising. The step of rinsing the region may also take place in vivo on a region of biological tissue of a patient.

Physical manipulation of the neoplastic tissue may comprise a variety of procedures including: applying radioactive material to the neoplastic portion; applying a cryogenic agent to the neoplastic portion; applying heat to the neoplastic portion such as thermal ablation; extirpation of the tissue; applying electrical current to the neoplastic portion; applying a chemotherapy drug to the neoplastic portion; applying a gene therapy treatment to the neoplastic portion; radiation of the tissue; implantation of the tissue with therapeutic delivery systems; irradiating the neoplastic portion with radiation having a wavelength corresponding to a photoactivatable cytotoxic agent; any other methods which would lead to the elimination of the abnormal area.

Means useful to select the neoplastic portion for physical manipulation include: a visual display; a head mounted display; a system for projecting the information directly onto the operative field of view; and a system for projecting the information directly on the retinal of the operator.

Means or tools useful for the physical manipulation of the neoplastic and non-neoplastic tissue include: a cryotherapy probe; a radiation treatment applicator; an electronic surgical cutting tool; a laser used to ablate tissue; and a thermal applicator to apply localized heat to the sample.

The physical manipulation of the neoplastic portion may also take place in a variety of settings in which a manipulation of abnormal tissue may occur. The settings may include but are not solely limited to one of the following: an operating room; a procedure room; a radiology or radiation oncology suite; or a medical practioner's office.

Figure 2:
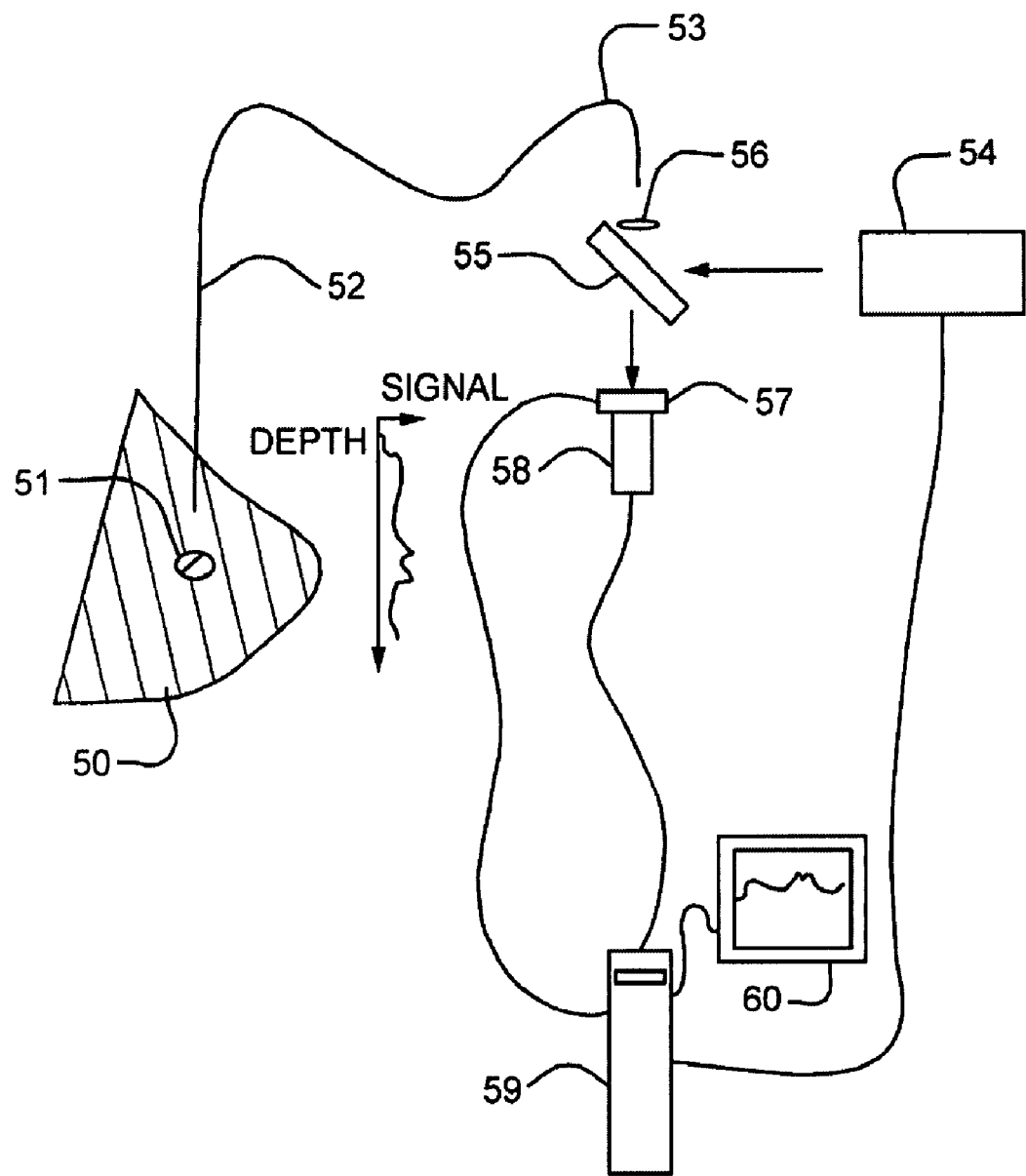
FIG. 2 illustrates an embodiment of the present invention.

An in vivo embodiment of the invention, for examining biological tissue 50 to differentiate the boundary between neoplastic 51 and non-neoplastic tissue is illustrated in FIG. 2. An endoscope or other instrument 52 is used to introduce light carried by an optical fiber 53 from a monochromatic light source 54. A dichroic mirror 55 and lens 56 are shown schematically for introducing the light into the fiber 53. Raman light from the biological tissue is carried from the tissue back through the lens 56 and mirror 55, through a filter 57 to a detector 58. The signal from the detector 58 is analyzed by a computer system 59 and displayed on a monitor 60.

Filter 57 is most preferably an Evan's split element liquid crystal tunable filter, which is controlled by computer 59.

The endoscope 52 is preferably an imaging endoscope or fiberscope, where light is conducted from the tissue to the detector 58 in a coherent manner through a large plurality of optical fibers. A series of two dimensional images is preferably taken as a function of depth into the tissue and of the Raman shifted wavelength.

EXAMPLE

A typical operating scenario for this approach is to use an image recording device such as a CCD camera or CMOS based digital imaging system to record an image of the light which emanates from the operative field of view. The recording of the light must be performed in a way that allows spectral resolution of Raman scattering features characteristic of the materials, in this case tissues, in the field of view. A typical approach to record such an image is to use a CCD or CMOS detector to detect light which has passed through a narrowband tunable filter. Several types of tunable filters can be used to filter the light prior to detection including Liquid Crystal Tunable Filter (LCTF), Acousto-Optic Tunable Filter (AOTF), Multi Conjugate Filter (MCF). Images are recorded at distinct set points of the tunable filter and treated as a stack of images in spectral space, known in the art as a hyperspectral image. There are alternative approaches to generate a hyperspectral image including Computed Tomography Imaging Spectroscopy (CTIS) which can be employed if the alternative approaches have the spectral resolution to resolve Raman features (typically less than 20 $cm^{-1}$).

In order to generate discernable Raman scatter the field of view which is the focus of study must be illuminated by a substantially monochromatic source such as a laser.

In addition to the hyperspectral image of the field of view with high spectral resolution, a low spectral resolution image such as is obtained under the illumination of broadband light can also be acquired. This can be obtained for instance with "white light" illumination and a standard color digital imaging camera.

The data from the hyperspectral image is processed to account for measurement artifacts including wavelength dependent transmission and detection variations caused by the optics and detectors. This is performed in standard fashion by making a measurement of the optical characteristic of the measurement system using known standards and determining the optical performance of the whole system.

After instrument response correction of the raw data, the spectroscopic features within the pixels which comprise the image are used to create an image which can guide the operator in terms of the location of (non-neoplastic), or neoplastic tissue. Creation of this guide image involves application of one or more of different data processing technique collectively known as multivariate approaches. These include techniques such as principal component analysis (PCA), Cosine Correlation Analysis (CCA), Euclidian Distance Analysis (EDA), multivariate curve resolution (MCR), Band T. Entropy Method (BTEM) Mahalanobis Distance (MD), Adaptive Subspace Detector (ASD) to name exemplary modes. Substantially any method which takes advantage of the spectral information in the hyperspectral image could be employed.

In some cases multivariate methods are employed on a dataset and can be used without the dependence on an external reference sample. In other cases multivariate methods can be used to interpret data based on some reference information. In a typical example of this approach, the distinctive spectral differences between neoplastic and normal brain tissue can be used as a basis for applying multivariate techniques to classify each pixel in an image as normal or neoplastic tissue.

Once the raw hyperspectral data is instrument corrected and interpreted, using multivariate techniques, it can be fused with the normal "white light" image of the field of view. This enables the operator to see an image of the operative field of view with information about neoplastic state mapped, for example, in a particular color.

Figure 3A:
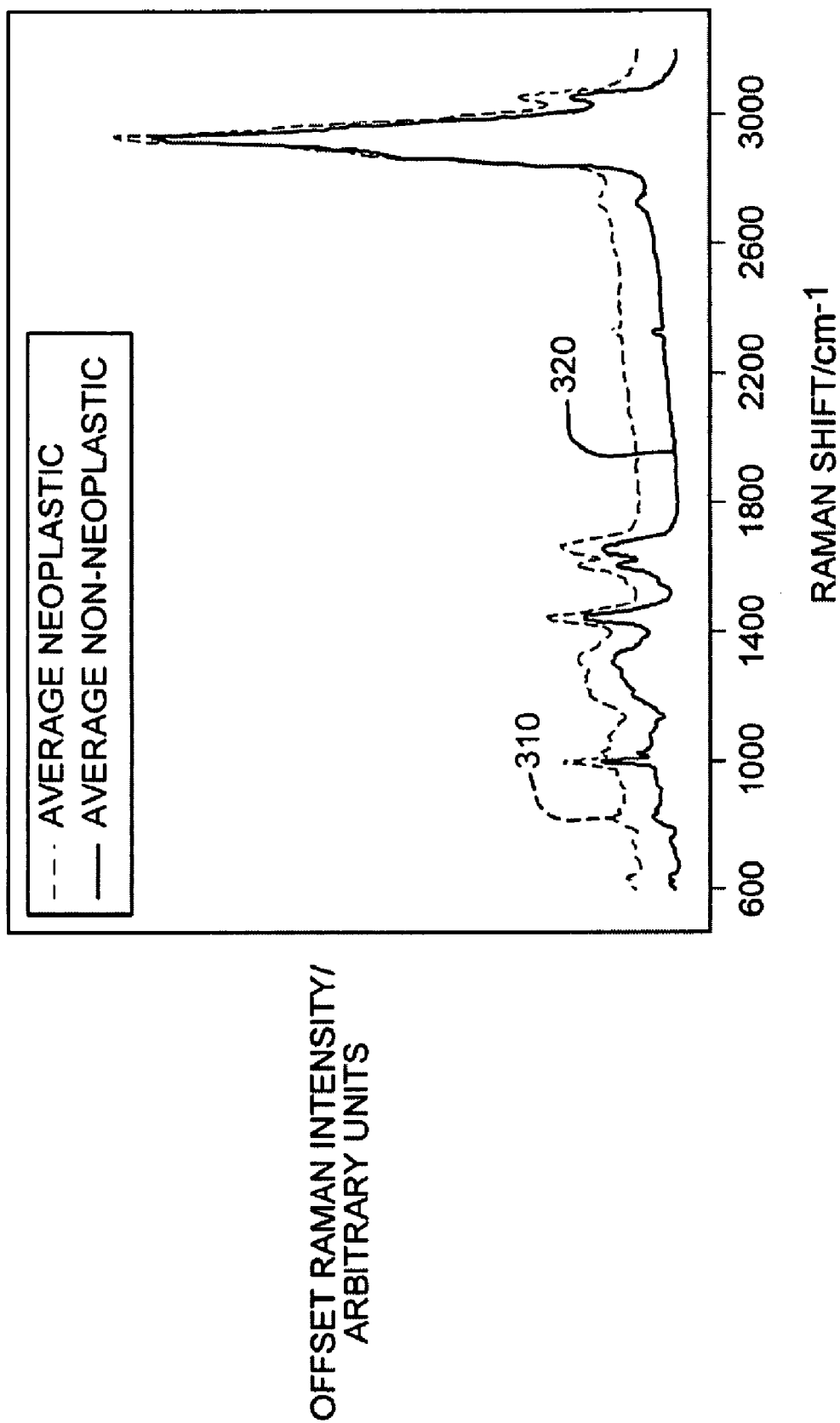
FIGS. 3A and 3B illustrate an average Raman dispersive spectrum of non-neoplastic and neoplastic tissue and the principal component analysis scores plot demonstrating the ability to distinguish between non-neoplastic and neoplastic tissue.
Figure 3B:
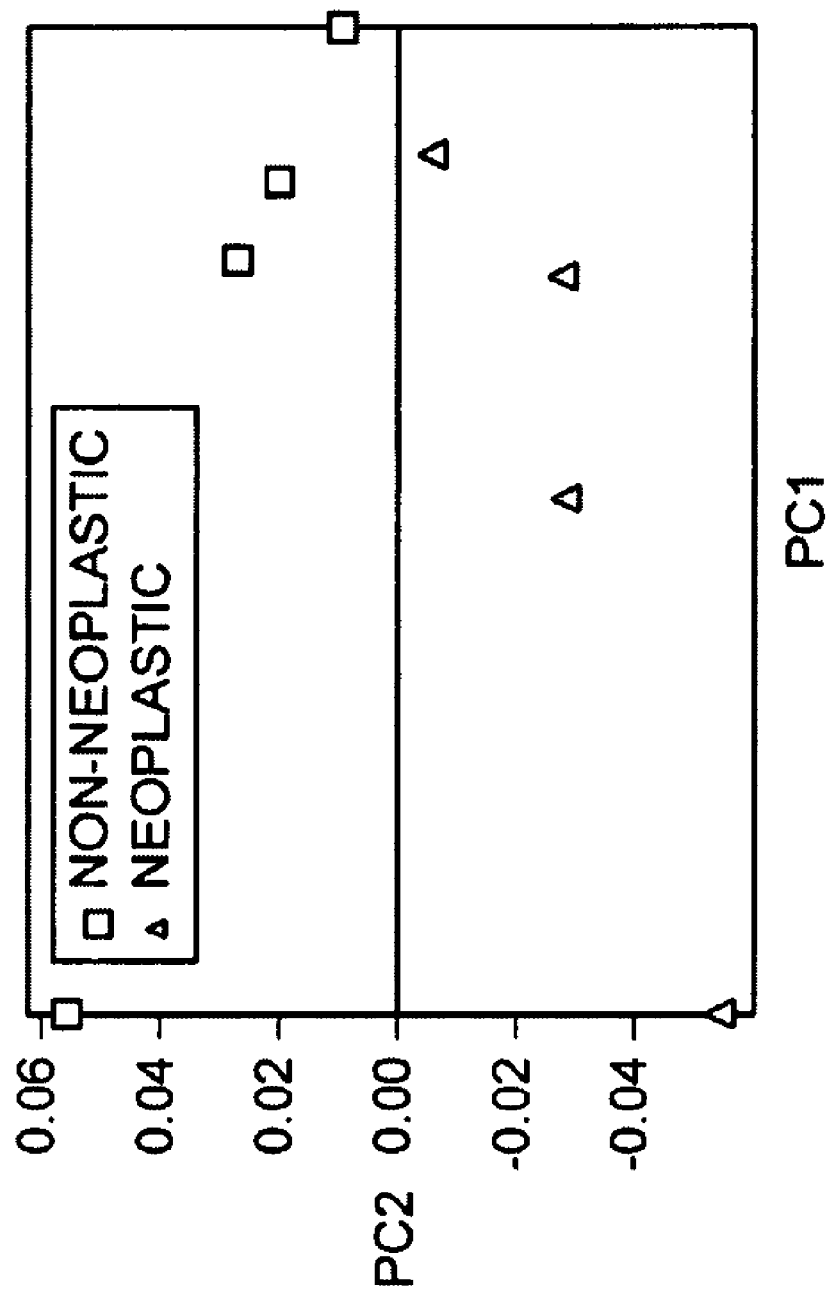

FIG. 3A compares the Raman dispersive spectra of neoplastic and areas of non-neoplastic brain tissue. Each spectrum is an average of 5 replicates. Brain tissue samples were removed during routine surgery and prepared using standard sample preparation techniques, including paraffin embedding and microtome sectioning. Sections were placed on aluminum-coated microscope slides and the paraffin removed using standard methods. Spectrum 310 corresponds to neoplastic tissue and spectrum 320 corresponds to non-neoplastic tissue. FIG. 3B is the Principal Component analysis score plot of this data, demonstrating that the two sets of data are distinguishable.

Figure 4:
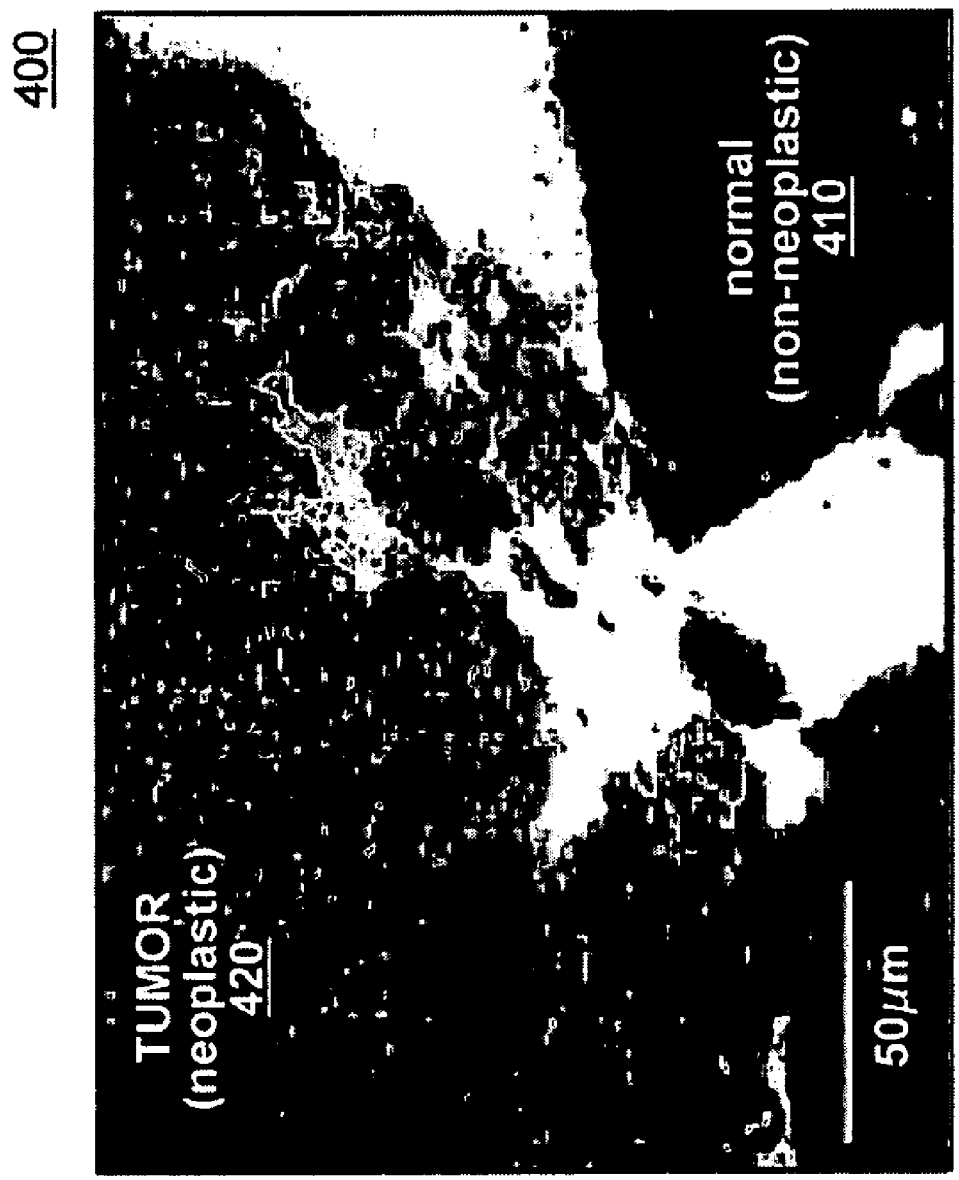
FIG. 4 illustrates a microscopic view of non-neoplastic and neoplastic brain tissue.

FIG. 4 shows a microscopic view 400 of brain tissue which was prepared as described for FIGS. 3A and 3B. In this section, there are clear areas of neoplastic tissue 420 and areas of non-neoplastic tissue 410 as indicated by a pathologist. Although this tissue in particular was not imaged, the data illustrated in FIGS. 3A and 3B indicate that neoplastic and areas of non-neoplastic tissue have different Raman signals, and would be distinguishable in an image such as FIG. 4.

Figure 5:
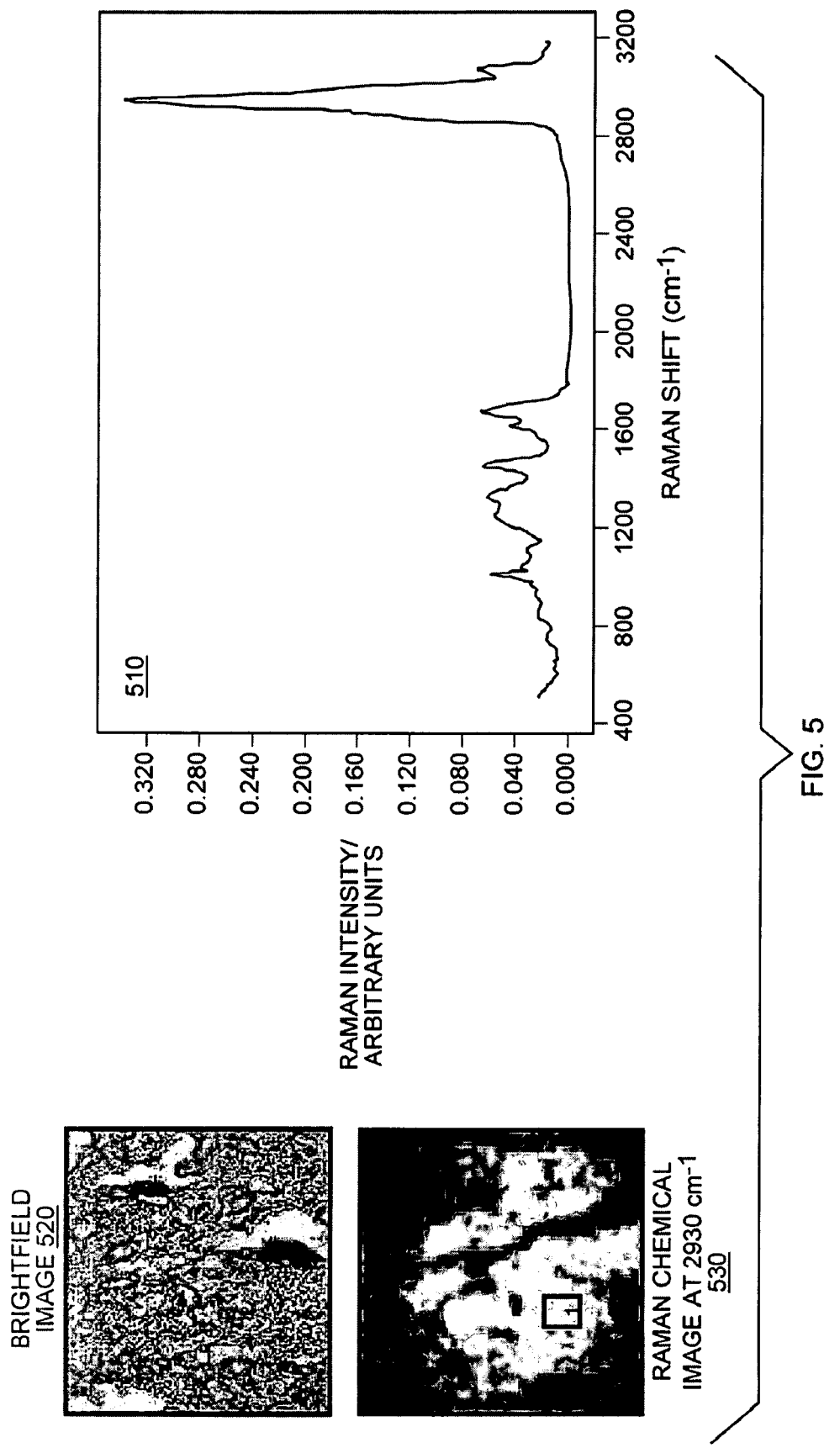
FIG. 5 illustrates a Raman chemical image of neoplastic brain tissue.

FIG. 5 illustrates a Raman chemical image of neoplastic brain tissue which was prepared as described for FIGS. 3A and 3B. Image 520 corresponds to the bright field image of the irradiated brain tissue and image 530 corresponds to the Raman chemical image at 2930 cm$^{-1}$. The Raman chemical image is derived from the distinct spectral Raman data 510 for the neoplastic brain tissue.

The above example can be carried out using a system comprising: a substantially monochromatic light source coupled to a means for light delivery which directs the light to the region containing a biological tissue: a Raman spectrometer system with or without imaging capability optically coupled to the region of interest and capable of acquiring measurements of Raman scattered light from the region: a software module for differentiating a boundary between neoplastic portion and non-neoplastic portion in the region based on evaluation of measurements of Raman spectroscopic measurements: a module, such as a visual display which depicts the region on a screen, for allowing selection of the distinctive portions for manipulation. Such a system can further comprise a broadband illumination and image capture channel to facilitate display of the Raman based information in the context of the visual appearance of the region of interest. Operative tools consistent with a desired manipulation may be integrated into the system.

In one embodiment, the system would comprise 532 nm laser coupled to a laser delivery fiber with a short pass scrub filter at the distal end to remove any contribution of the fiber to the illumination light directing substantially monochromatic light to a region of tissue. Integrated into this delivery fiber is a fiber based light collection system which collects light emanating from the field of view while blocking the illumination light from entering the collecting fiber. The output of the collection fiber is coupled to a Liquid Crystal Tunable Filter. The output of the LCTF is coupled to a cooled CCD camera for data acquisition. A software module controls data acquisition and processing rendering an image of the region of tissue which carries information about the spatial distribution of neoplastic and non-neoplastic tissue within the region. A LCD display system displays the rendered image in a fashion that the operator is allowed to select neoplastic tissue for manipulation using operative manipulative tools such as a scalpel.

The present disclosure may be embodied in other specific forms without departing from the spirit or essential attributes of the disclosure. Accordingly, reference should be made to the appended claims, rather than the foregoing specification, as indicated the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed is:

1. A method for chemical imaging to determine tissue margins during surgery comprising:
   irradiating, with a substantially monochromatic light, a region containing a biological tissue;
   obtaining a Raman spectroscopic image from the irradiated region for at least one Raman spectroscopic value characteristic of either a neoplastic portion or a non-neoplastic portion in the region containing the biological tissue, wherein said Raman spectroscopic image comprises spectral information recorded at each pixel in the image;
   differentiating a boundary between the neoplastic portion and the non-neoplastic portion in the region containing the biological tissue, wherein said differentiating comprises analyzing said spectral information recorded at each pixel of said Raman spectroscopic image using a method selected from the group consisting of: principal component analysis (PCA), Cosine Correlation Analysis (CCA), Euclidian Distance Analysis (EDA), multivariate curve resolution (MCR), Band T. Entropy Method (BTEM), Mahalanobis Distance (MD), Adaptive Subspace Detector (ASD), and combinations thereof;
   displaying a location of said boundary in said Raman spectroscopic image based on the results of the differentiating and
   selecting the neoplastic portion for physical manipulation, wherein said selecting is based on the displayed boundary location between the neoplastic portion and the non-neoplastic portion.

2. The method of claim 1, wherein said differentiating includes correlating the Raman spectral image with a visible image of the region.

3. The method of claim 1, wherein said at least one Raman spectroscopic value includes a Raman shift for one of the following:
   the neoplastic portion; and
   the non-neoplastic portion.

4. The method of claim 1, wherein said biological tissue comprises neurological tissue.

5. The method of claim 1 further comprising physically manipulating
   the neoplastic portion.

6. The method of claim 5, wherein physically manipulating the neoplastic portion comprises excising the neoplastic portion from the region containing said biological tissue.

7. The method of claim 6, wherein the steps of differentiating, selecting, and excising the selected neoplastic portion are performed iteratively.

8. The method of claim 6, wherein the steps of differentiating, selecting and excising the selected neoplastic portion are performed iteratively and in vivo on the region of biological tissue of the patient.

9. The method of claim 6, further comprising rinsing the region containing biological tissue between the steps of selecting and excising.

10. The method of claim 9, wherein the step of rinsing the region containing biological tissue between the steps of selecting and excising is performed in vivo on the region of biological tissue of the patient.

11. The method of claim 5, wherein the step of physically manipulating of the neoplastic portion is performed in vivo on the region of biological tissue of a patient.

12. The method of claim 5, wherein physically manipulating the neoplastic portion comprises one of the following:
   applying radioactive material to the neoplastic portion;
   applying a cryogenic agent to the neoplastic portion;
   applying heat to the neoplastic portion;
   applying electrical current to the neoplastic portion;
   applying a chemotherapy drug to the neoplastic potion;
   applying a gene therapy treatment to the neoplastic portion; and
   irradiating the neoplastic portion with radiation having a wavelength corresponding to a photoactivatable cytotoxic agent.

13. The method of claim 12, wherein the step of physically manipulating the neoplastic portion is performed in vivo on a region of tissue on the patient.

14. The method of claim 5, wherein the step of physically manipulating the neoplastic portion takes place in one of the following: a neurological operating room; a neurological procedure room; a radiology suite; and a medical practitioner's office.

15. The method of claim 1 further comprising the steps of:
    selecting the non-neoplastic portion for physical manipulation; and
    physically manipulating the non-neoplastic portion.

16. A method for chemical imaging to determine tissue margins during surgery comprising:
    irradiating, with a substantially monochromatic light, a region containing a neurological tissue;
    obtaining Raman spectroscopic data from endogenous molecules in the irradiated region, wherein said Raman spectroscopic data comprises spatially resolved Raman spectroscopic data;
    differentiating a boundary between the neoplastic portion and the non-neoplastic portion in the region containing the neurological tissue wherein said differentiating comprises
        analyzing said spatially resolved Raman spectroscopic data in at least one direction for at least one Raman spectroscopic value characteristic of either endogenous molecules of the neoplastic portion or endogenous molecules of the non-neoplastic portions,
        wherein said analyzing comprises using a method selected from the group consisting of: principal component analysis (PCA), Cosine Correlation Analysis (CCA), Euclidian Distance Analysis (EDA), multivariate curve resolution (MCR), Band T. Entropy Method (BTEM), Mahalanobis Distance (MD), Adaptive Subspace Detector (ASD), and combinations thereof; and
    selecting the neoplastic portion for physical manipulation based on the differentiation of the boundary between the neoplastic portion and the non-neoplastic portion.

17. The method of claim 16, wherein said differentiating includes correlating the Raman spectral data with a visible image of the region.

18. The method of claim 16 further comprising physically manipulating
    the neoplastic portion.

19. The method of claim 16, wherein the step of physically manipulating the neoplastic portion is performed in vivo on the region of neurological tissue of a patient.

20. The method of claim 16 further comprising the steps of:
    selecting the non-neoplastic portion for physical manipulation; and
    physically manipulating the non-neoplastic portion.

21. A system comprising:
    a substantially monochromatic light source irradiating, a region containing a biological tissue;
    a Raman spectrometer for obtaining Raman spectroscopic image data from the irradiated region for at least one Raman spectroscopic value characteristic of either a neoplastic portion or a non-neoplastic portion in the region containing the biological tissue, wherein said Raman spectroscopic image comprises spectral information recorded at each pixel in the image;
    means for differentiating a boundary between the neoplastic portion and the non-neoplastic portion in the region containing the biological tissue by analyzing said spectral information recorded at each pixel of said the Raman spectroscopic image using a method selected from the group consisting of: principle component analysis (PCA), Cosine Correlation Analysis (CCA), Euclidian Distance Analysis (EDA), multivariate curve resolution (MCR), Band T. Entropy Method (BTEM), Mahalanobis Distance (MD), Adaptive Subspace Detector (ASD), and combinations thereof;
    means for displaying a location of said boundary in said Raman spectroscopic image; and
    means for allowing selection of the neoplastic portion for physical manipulation based on the differentiation and the display of the boundary between the neoplastic portion and the non-neoplastic portion.

22. The system of claim 21 further comprising:
    means for physically manipulating
    the neoplastic portion.

23. The system of claim 21 further comprising:
    means for physically manipulating the neoplastic portion.

* * * * *